United States Patent
Yeon et al.

(10) Patent No.: US 8,016,992 B2
(45) Date of Patent: Sep. 13, 2011

(54) REFERENCE ELECTRODE INCLUDING ELECTROLYTE CONTAINING OPTICALLY-ACTIVE MATERIAL AND AUTOMATIC ELECTROCHEMICAL POTENTIAL CORRECTION APPARATUS USING THE SAME

(75) Inventors: Jei-Won Yeon, Daejeon (KR); In-Kyu Choi, Daejeon (KR); Won-Ho Kim, Daejeon (KR); Kyuseok Song, Daejeon (KR)

(73) Assignees: Korea Atomic Energy Research Institute, Daejeon (KR); Korea Hydro and Nuclear Power Co., Ltd., Seoul (KR)

( * ) Notice: Subject to any disclaimer, the term of this patent is extended or adjusted under 35 U.S.C. 154(b) by 315 days.

(21) Appl. No.: 12/470,838

(22) Filed: May 22, 2009

(65) Prior Publication Data

US 2009/0288949 A1    Nov. 26, 2009

(30) Foreign Application Priority Data

May 26, 2008   (KR) .................. 10-2008-0048384

(51) Int. Cl.
G01N 27/333  (2006.01)
G01N 27/26   (2006.01)
G01N 21/01   (2006.01)

(52) U.S. Cl. ........ 204/435; 204/433; 204/416; 204/406; 204/407; 204/400; 422/50; 422/400; 422/401; 422/402; 422/403; 422/62; 422/68.1; 422/82.01; 422/82.05; 422/82.09

(58) Field of Classification Search .............. 204/416, 204/433, 435, 400, 406, 407; 422/50, 400, 422/401, 402, 403, 62, 68.1, 82.01, 82.05, 82.09

See application file for complete search history.

(56) References Cited

U.S. PATENT DOCUMENTS 4,822,456 A    4/1989    Bryan

FOREIGN PATENT DOCUMENTS

| KR | 100152426 A | 6/1998 |
| KR | 1020000002919 A | 5/2000 |
| KR | 1020020017120 A | 3/2002 |
| KR | 1020020094701 A | 12/2002 |
| KR | 1020030038000 A | 5/2003 |
| KR | 1020040020350 A | 3/2004 |
| KR | 1020060046932 A | 5/2006 |
| WO | 8907758 A1 | 8/1989 |

*Primary Examiner* — Bruce Bell
(74) *Attorney, Agent, or Firm* — Fredrikson & Byron, PA

(57) ABSTRACT

Disclosed herein is a reference electrode including an electrolyte containing an optically-active material, including: an electrode body provided at an end thereof with an electrolyte separation membrane and charged therein with an optically-active material and an electrolyte solution; an inner electrode disposed in the electrode body to be immersed in the electrolyte solution; and an absorbance measurement probe for transmitting light to the electrolyte solution and collecting reflected light waves, which is disposed in the electrode body to be immersed in the electrolyte solution. Since the concentration of an electrode reaction material, such as $Cl^-$, in the electrolyte is calculated using the absorbance of the electrolyte solution containing the optically-active material, the change in potential of the reference electrode can be properly corrected even when the reference electrode is exposed to a test environment for a long period of time and thus the concentration of the electrolyte changes. Thus, the functions of the reference electrode can be maintained for a long period of time, thereby rapidly monitoring the abnormal states caused by damage to the reference electrode.

20 Claims, 7 Drawing Sheets

PRIOR ART

REFERENCE ELECTRODE INCLUDING ELECTROLYTE CONTAINING OPTICALLY-ACTIVE MATERIAL AND AUTOMATIC ELECTROCHEMICAL POTENTIAL CORRECTION APPARATUS USING THE SAME

CROSS REFERENCE TO RELATED APPLICATION(S)

This application claims the benefit of Korean Patent Application No. 2008-0048384, filed on May 26, 2008, entitled "REFERENCE ELECTRODE CONTACTING LIGHT ABSORBED CHEMICALS IN THE ELECTROLYTE AND AUTOMATIC ELECTROCHEMICAL POTENTIAL CORRECTION APPARATUS USING THE SAME," which is hereby incorporated by reference in its entirety into this application.

BACKGROUND OF THE INVENTION

1. Field of the Invention

The present invention relates to a reference electrode and an automatic electrochemical potential correction apparatus using the same, and, more particularly, to a reference electrode including an electrolyte containing an optically-active material, which can maintain accuracy for a long period of time in the electrochemical measurement, and an automatic electrochemical potential correction apparatus using the same.

2. Description of the Related Art

In order to measure and control chemical or electrochemical reactions occurring in liquid media, such as aqueous solutions, organic solutions, high-temperature molten salts and the like, electrochemical methods have been widely used from the late 19$^{th}$ century up to the present. Particularly, from the late 20$^{th}$ century, research and development in the field of secondary lithium batteries, fuel cells and solar cells has been enlarged, so that the demand for using the electrochemical methods is increasing rapidly.

In the electrochemical methods, in order to accurately measure and control the potential of a working electrode, it is necessarily required to use a reference electrode. Generally, the reference electrode is fabricated using an electrode reaction in which an oxidation-reduction reaction appears clearly in a narrow potential region.

Typical electrode reactions used to fabricate a reference electrode are as follows (Bard, A. J. & L. R. Faulkner, Electrochemical Methods: Fundamentals and Applications. New York: John Wiley & Sons, 2nd Edition, 2000).

$2H^+ + 2e^- \leftrightarrows H_2$ (Pt); Standard hydrogen electrode (SHE) ($E°=0.0V$)

$AgCl + e^- \leftrightarrows Ag + Cl^-$; Silver-Silver Chloride Electrode ($E°=0.225V$ saturated)

$Hg_2^{2+} + 2e^- \leftrightarrows 2Hg$, $Hg_2^{2+} + 2 Cl^- \leftrightarrows Hg_2Cl_2$; Saturated calomel electrode (SCE) ($E°=+0.242V$ saturated)

$Cu^{2+} + 2e^- \leftrightarrows Cu$; Copper-copper(II) sulfate electrode ($E°=-0.318V$)

Among the electrode reactions, although the first electrode reaction, which is a reduction reaction of hydrogen ions to hydrogen gases, is a standard reaction ($E°=0.0$ V), it is scarcely used practically because hydrogen gases must be treated.

FIG. 1 is a sectional view showing a conventional reference electrode.

Referring to FIG. 1, the conventional reference electrode includes an electrode body provided at the end thereof with an electrolyte separation membrane 11, an inner electrode 20 provided in the electrode body, and an electrolyte 30 charged in the electrode body such that the inner electrode 20 is partially immersed therein.

Generally, in a reference electrode most frequently used in the field of research and industries, the inner electrode 20 is an Ag/AgCl electrode or a calomel electrode. In this reference electrode, since it is required that the activity of chlorine ions (Cl$^-$) in the electrolyte 30 be constant, the concentration of chlorine ions (Cl$^-$) in the electrolyte 30 must also be maintained constant.

When natural water including underground water and river water or cooling water used in a heat exchanger system is monitored for a long period of time using an electrochemical measurement method, the reference potential of the reference electrode used in this monitoring can be gradually changed because the concentration of an electrolyte containing chlorine ions in the reference electrode is decreased due to the difference in concentration between the electrolyte and a test solution. Further, when the reference electrode is used to monitor natural water or cooling water for a long period of time, the reference electrode is damaged, so that the electrolyte charged in the reference electrode is contaminated, thereby providing an incorrect reference potential.

Korean Patent Registration No. 10-0477448-0000 (2005.03.09) discloses a microvalve for nanofluid flow control using a shape-memory alloy film, in which the microvalve is installed in an electrode system, thus minimizing the consumption of KCl (Cl$^-$). Further, Korean Patent Registration Nos. 10-0329393-0000 (2002.03.07) and 10-0483628-0000 (2005.04.07) disclose a reference electrode, in which the leakage of KCl present in the reference electrode is prevented by using a polymer material, thus improving the durability of the reference electrode. Furthermore, Korean Patent Registration No. 10-0612270-0000 (2006.08.07) discloses a reference electrode for high-pressure and high-temperature aqueous environments, in which the concentration of KCl is maintained constant by using a polymer electrolyte, and which constitutes an electrode system such that it can be used in high-pressure high-temperature aqueous environments.

In order to improve the stability of a reference electrode, the leakage of an electrolyte charged in the reference electrode may be minimized, or a device for automatically circulating the electrolyte may be installed in the reference electrode.

In an Ag/AgCl electrode, in order to recover silver chloride (AgCl), an oxidation current or potential is periodically applied to the Ag/AgCl electrode, thus regenerating the surface thereof.

U.S. Pat. No. 4,822,456 (1989.04.18) discloses a method of preventing the contamination of a reference electrode by forming junction in the reference electrode using a permeable membrane, and an apparatus for monitoring the contamination of an electrolyte charged in the reference electrode by measuring the change in potential between the inner and outer electrodes provided at the inside and outside of the junction.

PCT Publication Nos. WO 89/07758 (1989.08.24) and PCT/US 89/00628 (1989.02.15), and Korean Patent Registration Nos. 10-0152426-0000 (1998.06.26), 10-0411715-0000 (2003.12.05) and 10-0439645-0000(2004.06.30) disclose a technology of miniaturizing a reference electrode using a thin film technique in order to apply the reference electrode to the semiconductor field.

As described above, to date, the technical improvement in the field of a reference electrode has been accomplished by preventing the leakage of an electrolyte charged in the reference electrode or by miniaturizing the reference electrode.

However, there has been no attempt to improve the stability of a reference electrode and monitor the state of the reference electrode by adding a light-absorbing material to an electrode and then correcting the concentration of the electrolyte using a spectrometer in order to detect the change in concentration of the electrolyte, which influences the electrode reaction of the reference electrode.

SUMMARY OF THE INVENTION

Accordingly, the present invention has been made keeping in mind the above problems occurring in the prior art, and an object of the present invention is to provide a reference electrode comprising an electrolyte containing an optically-active substance, which can accurately determine a reference potential even when the reference electrode has been used for a long period of time by calculating the dilution degree of an electrolyte charged in the reference electrode through an absorbance measurement method even when the electrolyte charged in the reference electrode is diluted by adding the optically-active material, not an electrochemically-active material, to the electrolyte, and an automatic electrochemical potential correction apparatus using the same.

In order to accomplish the above object, an aspect of the present invention provides a reference electrode including an electrolyte containing an optically-active material, including: an electrode body provided at an end thereof with an electrolyte separation membrane and charged therein with an optically-active material and an electrolyte solution; an inner electrode disposed in the electrode body such that it is immersed in the electrolyte solution; and an absorbance measurement probe for transmitting light to the electrolyte solution and collecting reflected light waves, which is disposed in the electrode body such that it is immersed in the electrolyte solution.

In the reference electrode, the optically-active material may be a material containing a chemical component absorbing one or more selected from among infrared light, visible light and ultraviolet light.

The absorbance measurement probe may output light having a wavelength of 140~5000 nm.

The optically-active material may be present in an initial concentration of 10 wt % or less The absorbance measurement probe may be composed of one or more selected from among an optical fiber, an optical tube, an optical reflector, and an optical cell enabling light to permeate an electrolyte.

The inner electrode may be made of one or more materials selected from among metals, conductive nonmetals, metal chlorides, metal oxides and metal sulfides.

The metal and conductive nonmetal may include one or more selected from among silver (Ag), mercury (Hg), copper (Cu), platinum (Pt), gold (Au), nickel (Ni), titanium (Ti), zirconium (Zr), molybdenum (Mo), tungsten (W), glassy carbon and graphite.

Another aspect of the present invention provides an automatic electrochemical potential correction apparatus, including: a reference electrode including an electrode body provided at an end thereof with an electrolyte separation membrane and charged therein with an optically-active material and an electrolyte solution, an inner electrode disposed in the electrode body such that it is immersed in the electrolyte solution, and an absorbance measurement probe for transmitting light to the electrolyte solution and collecting reflected light waves, which is disposed in the electrode body such that it is immersed in the electrolyte solution; a spectrometer for measuring absorbance by analyzing spectra of light waves collected by the absorbance measurement probe; and a reference potential corrector for outputting correction signals related to a change in the reference potential of the reference electrode according to the absorbance measured by the spectrometer.

Still another aspect of the present invention provides an automatic electrochemical potential correction apparatus, including: a reference electrode including an electrode body provided at an end thereof with an electrolyte separation membrane and charged therein with an optically-active material and an electrolyte solution, and an inner electrode disposed in the electrode body such that it is immersed in the electrolyte solution; a light source transmitting light to the reference electrode; a light detector for collecting light waves emitted from the light source and passing through the electrolyte charged in the reference electrode; a spectrometer for measuring absorbance by analyzing spectra of the light waves collected by the light detector; and a reference potential corrector for outputting correction signals related to a change in the reference potential of the reference electrode according to the absorbance measured by the spectrometer.

In the automatic electrochemical potential correction apparatus, the optically-active material may be a material containing a chemical component absorbing one or more selected from among infrared light, visible light and ultraviolet light.

The reference potential corrector may calculate the change in concentration of the electrolyte using the absorbance measured by the spectrometer, and may calculate the change of reference potential due to the change in concentration of the electrolyte.

The reference potential corrector may calculate the change in the reference potential of the reference electrode using the linear relationship between the logarithmic value of the absorbance measured by the spectrometer and the reference potential of the reference electrode.

The light source may output light having a wavelength of 140~5000 nm.

The optically-active material may be present in an initial concentration of 10 wt % or less.

The spectrometer may measure the absorbance in a wavelength region of 150~2400 nm.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Hereinafter, preferred embodiments of the present invention will be described in detail with reference to the attached drawings.

Figure 1:
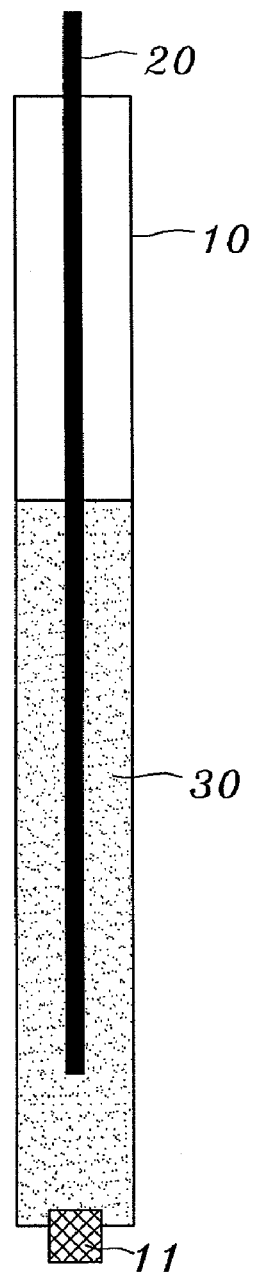
FIG. 1 is a sectional view showing a conventional reference electrode.
Figure 2:
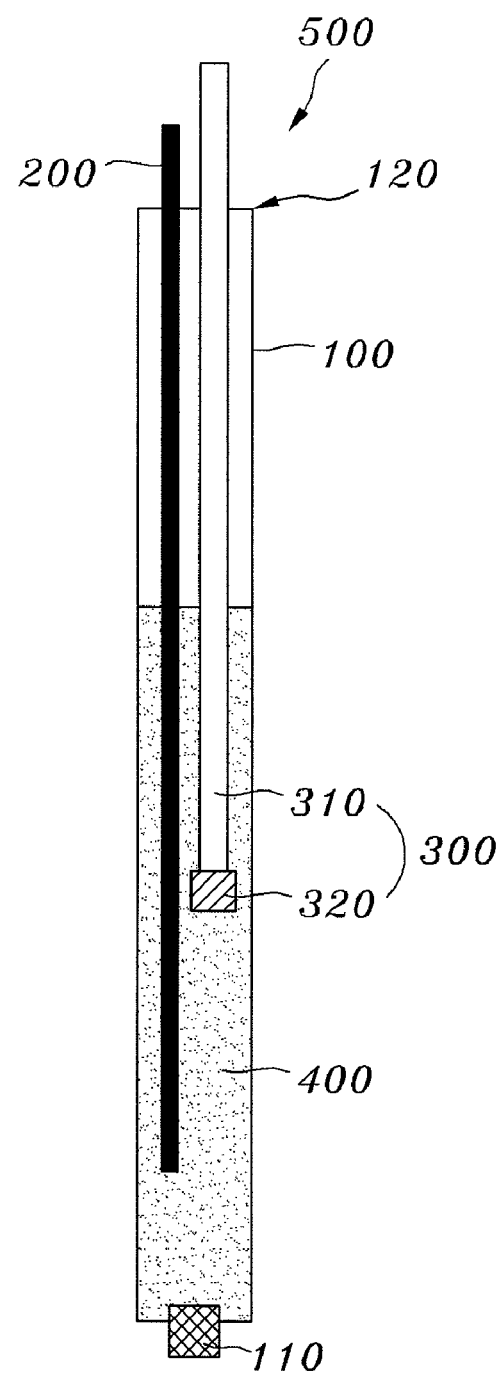
FIG. 2 is a sectional view showing a reference electrode having a function of automatically correcting a reference potential according to an embodiment of the present invention.

FIG. 2 is a sectional view showing a reference electrode having a function of automatically correcting a reference potential according to an embodiment of the present invention.

Referring to FIG. 2, a reference electrode including an electrolyte containing an optically-active material according to an embodiment of the present invention includes an electrode body 100; an inner electrode 200 and an absorbance measurement probe 300 disposed in the electrode body 100; and an electrolyte solution 400 containing an electrolyte and an optically-active material and charged in the electrode body 100.

The electrode body 100 is provided at one end thereof with an electrolyte separation membrane 110, and the electrolyte separation membrane 110 serves to prevent the electrolyte solution 400 from mixing with an external solution.

The electrode body 100 is provided at the other end thereof with a fixing part 120 in which the inner electrode 110 and the absorbance measurement probe 300 are inserted and fixed. The inner electrode 110 and the absorbance measurement probe 300 are fixed in the fixing part 120 such that they are spaced apart from each other at a predetermined interval.

The inner electrode 200 is made of one or more materials selected from among metals, conductive nonmetals, metal chlorides, metal oxides and metal sulfides.

Here, the metal and conductive nonmetal include one or more selected from among silver (Ag), mercury (Hg), copper (Cu), platinum (Pt), gold (Au), nickel (Ni), titanium (Ti), zirconium (Zr), molybdenum (Mo), tungsten (W), glassy carbon and graphite.

Preferably, the inner electrode 200 is made of one or more selected from among silver (Ag), mercury (Hg), copper (Cu), platinum (Pt), gold (Au), nickel (Ni), titanium (Ti), zirconium (Zr), molybdenum (Mo), tungsten (W), glassy carbon, and graphite, and, more preferably, one or more selected from among silver (Ag), mercury (Hg) and platinum (Pt)

The inner electrode 200 has one or more shapes selected from among rod, wire, tube, mesh, plate, thin layer and fiber shapes, and, preferably, one or more shapes selected from among rod, wire, tube and thin layer shapes.

The electrolyte includes one or more selected from among chlorides, sulfides and bromides, and, preferably, one or more selected from among potassium chloride (KCl) and sodium chloride (NaCl).

The optically-active material is a material containing a chemical component absorbing one or more selected from among infrared light, visible light and ultraviolet light.

The initial concentration of the optically-active material is 10 wt % or less, preferably 1.0 wt % or less, and more preferably 0.1 wt % or less, based on the electrolyte solution.

Generally, a spectrometer has a measurable concentration range. In the spectrometer, when an electrolyte solution has an excessively light color because it includes a very small amount of an optically-active material, measurement sensitivity is worsened, and even when an electrolyte solution has an excessively dark color because it includes a very large amount of an optically-active material, measurement accuracy is lowered because the measurable concentration range of the spectrometer has been exceeded (peaks interfere with each other). Therefore, when the concentration of the optically-active material is excessively high, the color of the electrolyte solution becomes excessively dark, so that it is difficult to accurately measure absorbance in a desired wavelength region. Further, when an excessively large amount of optically-active material is added to the electrolyte solution, the performance of a reference electrode can be deteriorated.

The absorbance measurement probe 300 is composed of one or more selected from among an optical fiber, an optical tube, an optical reflector, and an optical cell enabling light to permeate an electrolyte.

The light transmitted from the absorbance measurement probe 300 to the electrolyte may have a wavelength of 140~5000 nm. That is, the light may be infrared light, visible light or ultraviolet light.

Specifically, the absorbance measurement probe 300 may be composed of an optical fiber or tube 310 and an optical reflector 320 disposed at a position spaced apart from an end of the optical fiber or tube 310 by a predetermined distance. In FIG. 2, it is likely that the optical fiber 310 and optical reflector 320 are connected with each other, but, really, the optical fiber 310 and optical reflector 320 are spaced apart from each other by a predetermined distance. The electrolyte solution 400 including the optically-active material is charged in the space between the optical fiber 310 and the optical reflector 320.

In this case, the light emitted from the end of the optical fiber or tube 310 passes through the electrolyte solution 400 including the optically-active material charged between the optical fiber or tube 310 and optical reflector 320 and then reflected by the optical reflector 320, and then the reflected light is introduced into the optical fiber or tube 310.

The reference electrode may further include a temperature sensor for measuring the temperature of the electrolyte solution 400. Since the temperature of the electrolyte solution 400 is actually equal to that of the solution in which the reference electrode is placed, the temperature sensor may be additionally provided at the outside of the reference electrode.

Figure 3:
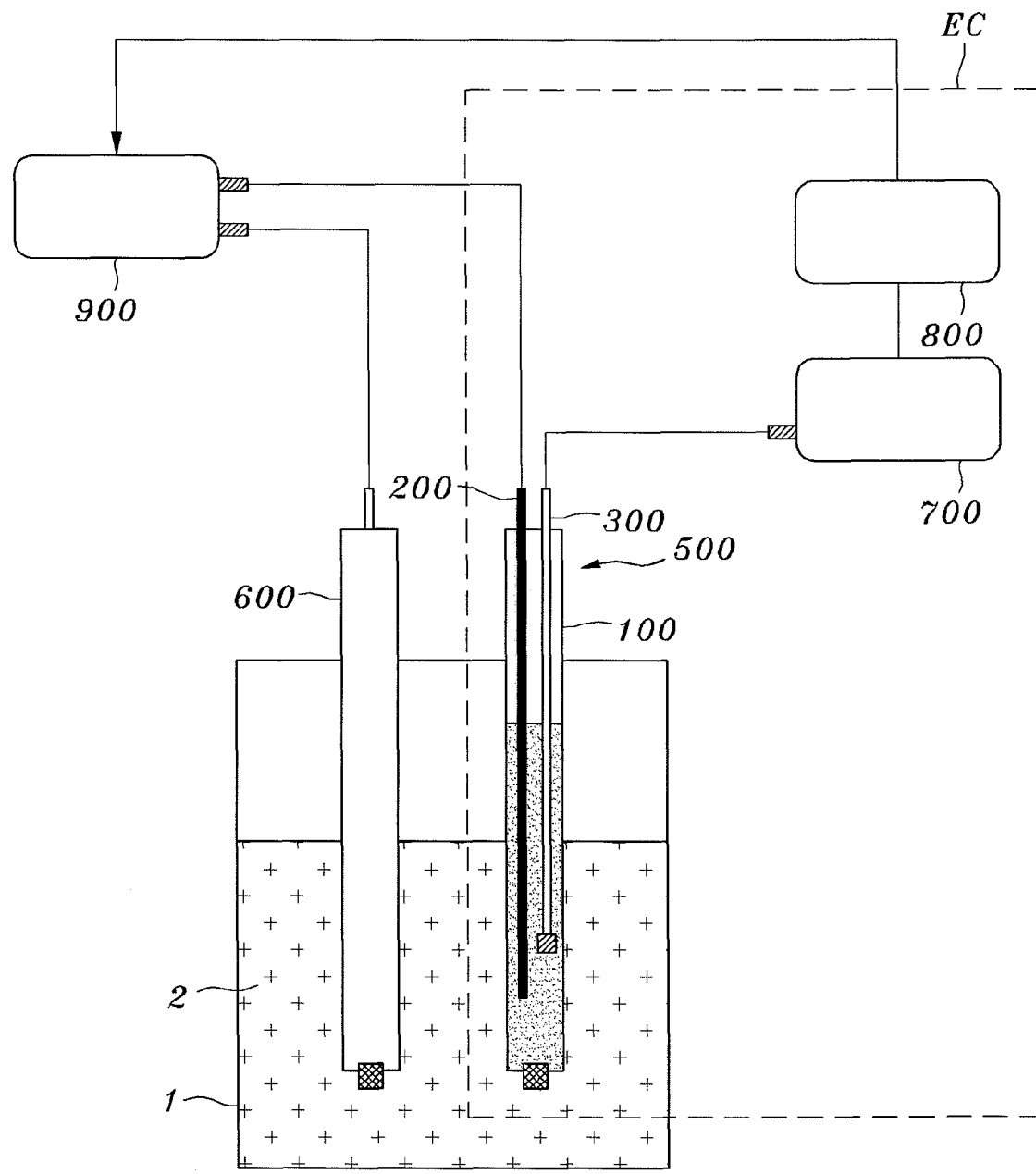
FIG. 3 is a schematic view showing an automatic electrochemical potential correction apparatus using the reference electrode according to a first embodiment of the present invention.

FIG. 3 is a schematic view showing an automatic electrochemical potential correction apparatus using the reference electrode according to a first embodiment of the present invention.

A reference electrode is referred to as an electrode which acts as a standard when a voltage is measured or applied in order to conduct electrochemical measurement, and an indicator electrode is referred to as an electrode which functions as a sensor. For example, when pH is to be measured, a pH electrode is an indicator electrode, and when ions are to be detected, an ion detection electrode is an indicator electrode.

Generally, when the voltage of the indicator electrode is measured to 1 V, it means that the voltage of the indicator electrode to the reference electrode (0 V) is 1 V. Therefore, the value of the indicator electrode changes depending on the subject to be measured, but that of the reference electrode does not change.

First, the basic theory will be explained as follows. The reference electrode generally used in the field of research and industry is an Ag/AgCl electrode or a calomel electrode. In this reference electrode, a reference potential changes depending on the concentration of potassium chloride (KCl), which is an electrolyte charged in the reference electrode. For example, in the electrode reaction of the Ag/AgCl electrode, as seen in the following Reaction Formula 1 and its Nernst Equation, the reference potential of the Ag/AgCl electrode is determined by the chemical activity ($a_{cl}$), which is an effective concentration of chlorine ions included in the electrolyte charged in the Ag/AgCl electrode.

AgCl+e⁻⇌Ag+Cl⁻;E°=0.222 V$_{SHE}$ $E_{Ag/AgCl} = E°_{Ag/AgCl} - 0.059 \log(a_{cl})$ [Reaction Formula 1]

Here, E is a reference potential considering the influence of chlorine ions, and E° is a standard potential of a reference electrode.

When a reference electrode is exposed to cooling water or natural water for a long period of time, the concentration of an electrolyte charged in the reference electrode is lowered, and thus its reference potential can change. Therefore, if the change in the concentration of the electrolyte can be spectroscopically measured using an optically-active material without influencing an electrode reaction (for example, AgCl+e⁻⇌Ag+Cl⁻), the change in the reference potential of the reference electrode due to the dilution of the electrolyte can also be calculated.

Figure 5:
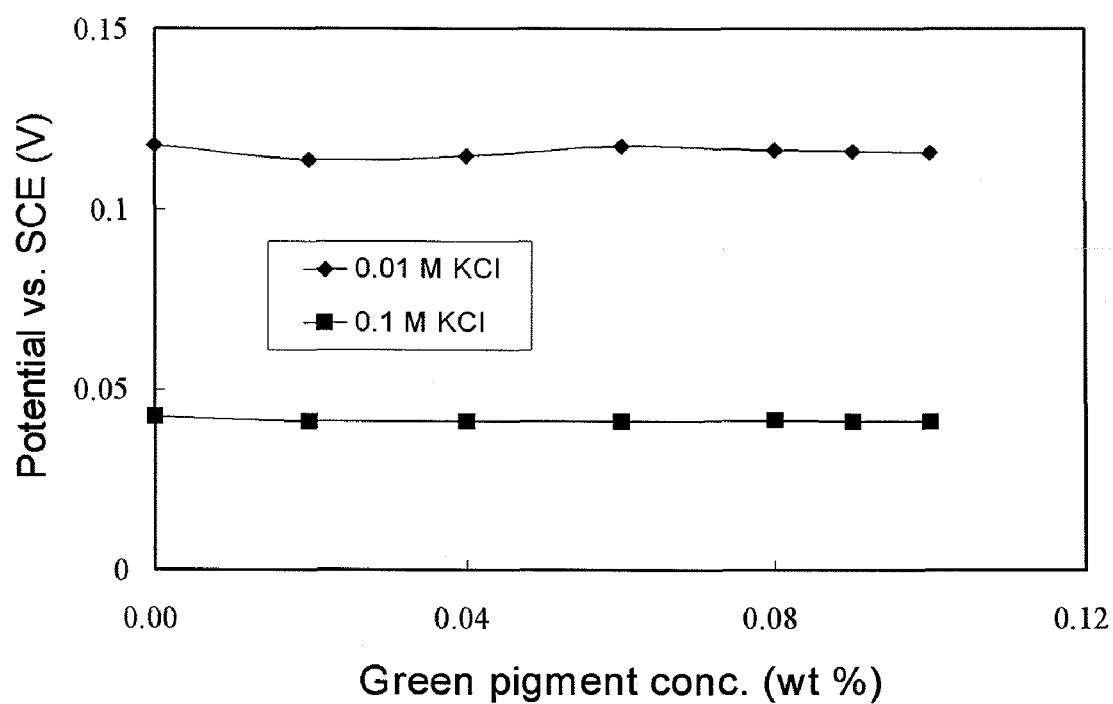
FIG. 5 is a graph showing the change in reference potential of an Ag/AgCl reference electrode to a saturated calomel electrode (SCE) when an optically-active material having various concentrations is added to an electrolyte (0.1 M and 0.01 M) in the Ag/AgCl reference electrode.

In this case, the optically-active material itself must not influence the potential of the reference electrode. From FIG. 5, it was found that the optically-active material does not influence the change of the potential of the reference electrode using the reference electrode in which the optically-active material is mixed in the electrolyte. FIG. 5 is a graph showing the change in the reference potential of the Ag/AgCl reference electrode to a saturated calomel electrode (SCE) when the optically-active material having various concentrations is added to the electrolyte (0.1 M and 0.01 M) in the Ag/AgCl reference electrode.

Figure 6:
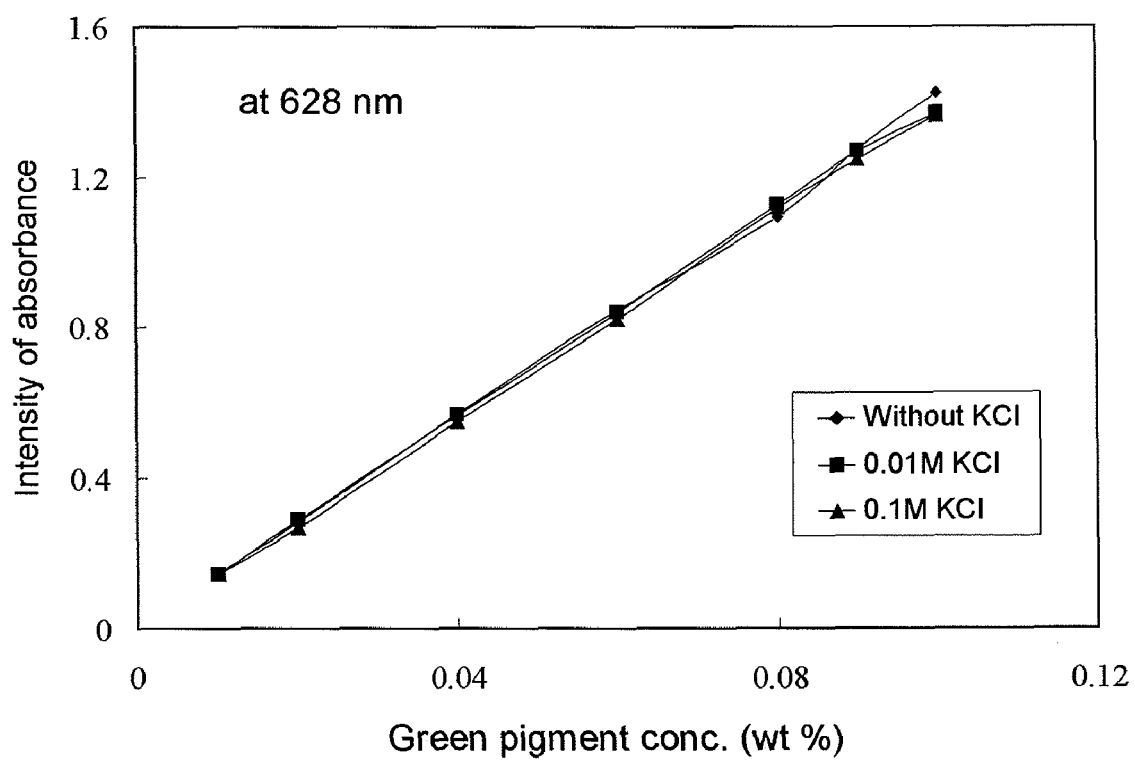
FIG. 6 is a graph showing the change in absorbance of a KCl media (an electrolyte) having various concentrations according to the concentration of an optically-active material.

Further, from FIG. 6, it can be seen that the absorbance of an electrolyte is influenced by only the optically-active material regardless of potassium chloride (KCl), which is the electrolyte. FIG. 6 is a graph showing the change in absorbance of a KCl media (an electrolyte) having various concentrations according to the concentration of an optically-active material As described above, it can also be seen that the change in the reference potential of the reference electrode can be calculated using the absorbance of the electrolyte diluted with optically-active material added to the electrolyte. Here, a green food color having absorbance characteristics at a wavelength of 628 nm is used as the optically-active material.

The automatic electrochemical potential correction apparatus according to a first embodiment of the present invention is represented by EC drawn with a dotted line in FIG. 3. The automatic electrochemical potential correction apparatus includes a reference electrode 500, a spectrometer 700 for measuring absorbance by analyzing spectra of light waves collected from the reference electrode 500, and a reference potential corrector 800 for outputting correction signals related to the change in the reference potential of the reference electrode 500 according to the absorbance measured by the spectrometer 700.

The reference electrode 500 includes an optically-active material, and is configured as shown in FIG. 2, as mentioned above.

Hereinafter, the automatic electrochemical potential correction apparatus according to a first embodiment of the present invention will be described in detail.

The reference electrode 500 includes: an electrode body 100 provided at one end thereof with an electrolyte separation membrane 110 and charged therein with an optically-active material and an electrolyte solution 400; an inner electrode 200 disposed in the electrode body 100 and immersed in the electrolyte solution 400; and an absorbance measurement probe 300 transmitting light to the electrolyte solution 400 and collecting reflected light waves, which is disposed in the electrode body and immersed in the electrolyte solution.

The spectrometer 700 serves to apply the light having a specific wavelength selected from among infrared light, visible light and ultraviolet light to the absorbance measurement probe 300.

The light applied to the absorbance measurement probe 300 has a wavelength of 140~5000 nm.

The light applied to the absorbance measurement probe 300 through the spectrometer 700 passes through an optical fiber 310 and the electrolyte solution 400 containing the optically-active material and is then reflected by an optical reflector 320, and then the reflected light waves are introduced into the optical fiber 310.

The spectrometer 700 measures absorbance by analyzing the spectra of the reflected light waves.

The wavelength region to be measured by the spectrometer 700 may be set according to the kind of optically-active material charged in the reference electrode.

For example, the wavelength region to be measured by the spectrometer 700 may be set to 150~2400 nm, preferably 200~1600 nm.

The reference potential corrector 800 serves to calculate the change in concentration of the electrolyte (the change in concentration of an electrode reaction material, for example, when the electrolyte is KCL, the change in concentration of Cl⁻) using the absorbance measured by the spectrometer 700, calculate the change of a reference potential due to the change in concentration of the electrolyte and then output correction signals for correcting the change of the reference potential.

Generally, with the passage of time, the concentration of an electrolyte is decreased, and thus the absorbance of an optically-active material is also decreased.

Therefore, the reference potential corrector 800 calculates the change in the reference potential of the reference electrode using the linear relationship between the logarithmic value of the absorbance measured by the spectrometer and the reference potential of the reference electrode, which are measured when the electrolyte is diluted and simultaneously the absorbance of the optically-active material decreases.

The reference potential corrector 600 finally transmits correction signals considering the change of the reference potential to an electrochemical measurement device 900.

The electrochemical measurement device 900 can accurately calculate the potential difference between the indicator electrode 600 and the reference electrode 500 in consideration of the correction signals by correcting the potentials measured by the indicator electrode 600 and the reference electrode 500.

In this case, in order to more accurately calculate the potential difference between the indicator electrode 600 and the reference electrode 500, a temperature sensor may further provided, thus allowing consideration of the effects of temperature.

Figure 4:
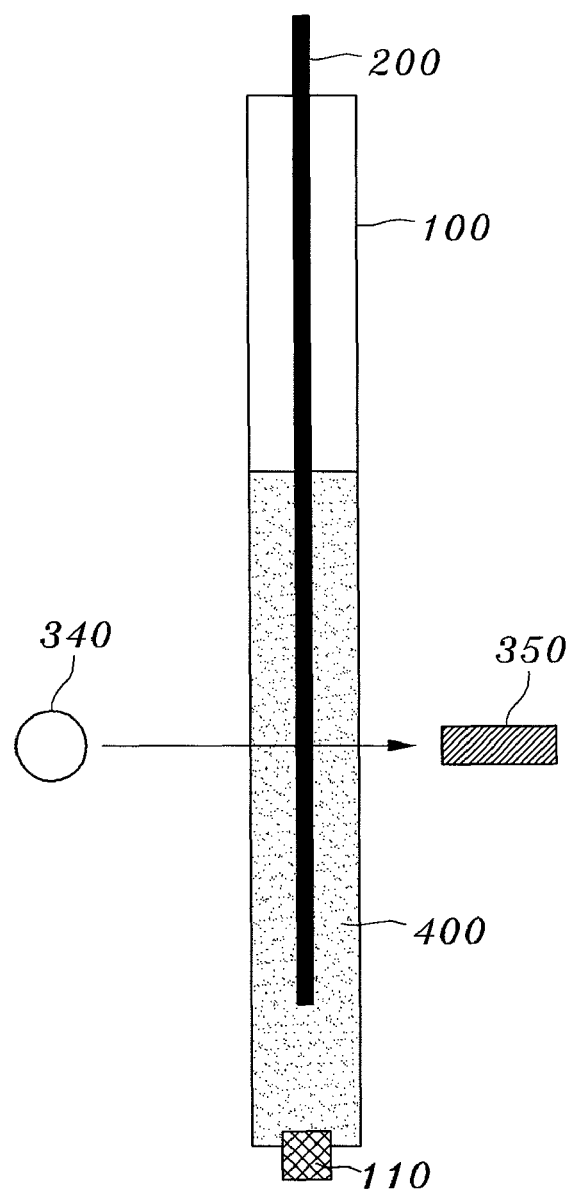
FIG. 4 is a schematic view showing an automatic electrochemical potential correction apparatus using the reference electrode according to a second embodiment of the present invention.

FIG. 4 is a schematic view showing an automatic electrochemical potential correction apparatus using the reference electrode according to a second embodiment of the present invention. In FIG. 4, only a reference electrode, a light source and a light detector are shown.

The automatic electrochemical potential correction apparatus according to a second embodiment of the present invention includes a reference electrode, a light source 340 transmitting light to the reference electrode, a light detector 350 for collecting the light waves emitted from the light source 340 and passing through an electrolyte charged in the reference electrode, a spectrometer for measuring absorbance by analyzing spectra of the light waves collected by the light detector 350, and a reference potential corrector for outputting correction signals related to the change in the reference potential of the reference electrode according to the absorbance measured by the spectrometer.

In this case, the reference electrode includes an electrode body 100 provided at one end thereof with an electrolyte separation membrane 110 and charged therein with an optically-active material and an electrolyte solution 400, and an inner electrode 200 disposed in the electrode body 100 and immersed in the electrolyte solution 400.

The automatic electrochemical potential correction apparatus according to a second embodiment of the present invention includes the light source 340 for emitting light and the light detector 350 for collecting the light waves passing through the electrolyte charged in the reference electrode instead of the absorbance measurement probe disposed in the reference electrode.

In this case, the light emitted from the light source 340 has a wavelength of 140~5000 nm, and the light waves collected by the light detector 350 are transmitted to the spectrometer.

In particular, since light having a predetermined wavelength must be transmitted from outside of the reference electrode to the electrolyte solution charged in the reference electrode body 120, the electrode body 120 of the reference electrode is made of a transparent material. Generally, the electrode body 120 may be made of quartz.

Figure 7:
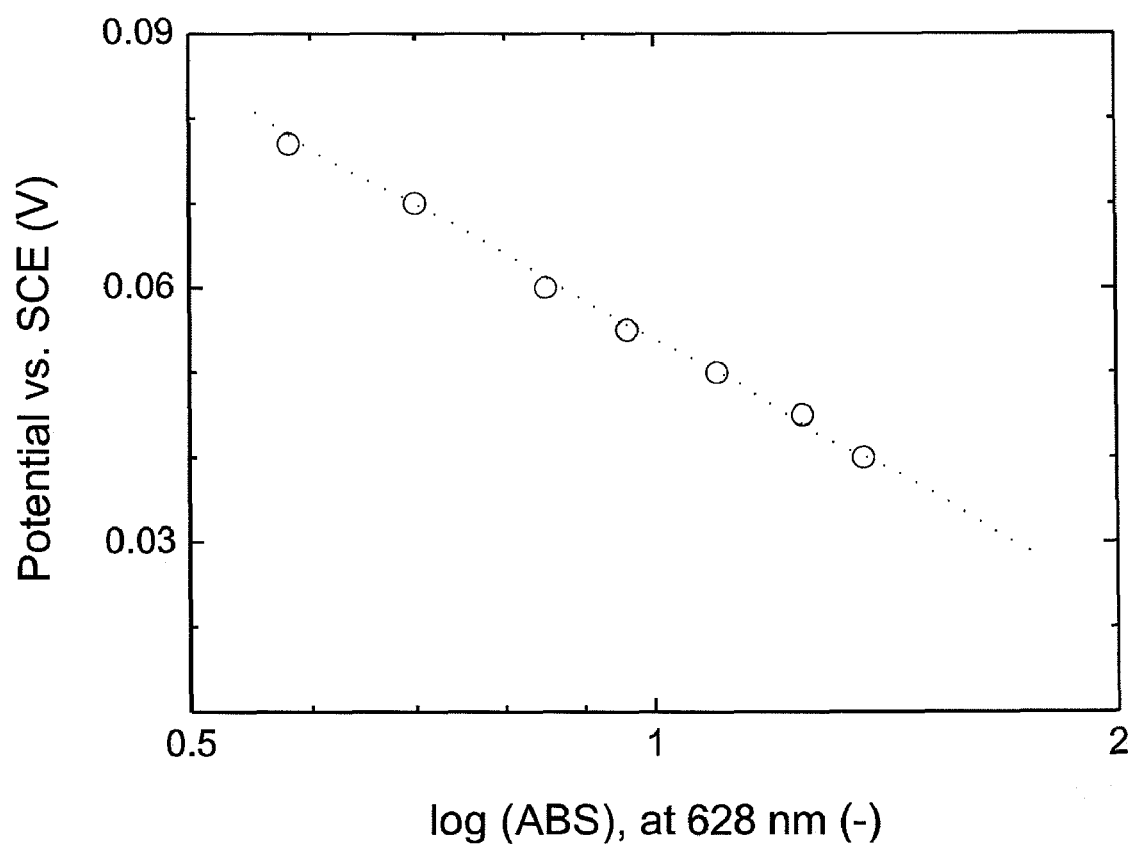
FIG. 7 is a graph showing the change in absorbance of an electrolyte (KCl) and the change in reference potential of an Ag/AgCl reference electrode to a saturated calomel electrode (SCE) when the electrolyte (KCl) is diluted from 0.1 M to 0.04 M.

FIG. 7 is a graph showing the change in absorbance of an electrolyte (KCl) and the change in reference potential of an Ag/AgCl reference electrode to a saturated calomel electrode (SCE) when the electrolyte (KCl) is diluted from 0.1 M to 0.04 M.

When a Ag/AgCl reference electrode in which a mixed solution of 0.1 M KCl and 0.1 wt % of a green food color (a green pigment) is used as an electrolyte was exposed to distilled water for a long period of time and thus the electrolyte charged in the Ag/AgCl reference electrode became diluted, the absorbance of the electrolyte at a wavelength of 628 nm and the potential difference between the Ag/AgCl reference electrode and the saturated calomel electrode (SCE) were respectively measured. From FIG. 7, it can be seen that there is a linear relationship between the logarithmic value of the absorbance of the optically-active material and the potential difference between the Ag/AgCl reference electrode and the saturated calomel electrode (SCE), which are measured when the electrolyte is diluted and simultaneously the absorbance of the optically-active material is decreased. As a result, it can be seen that, in the reference electrode charged therein with an electrolyte containing an optically-active material, the potential values changed due to the dilution of the electrolyte can be corrected by measuring the absorbance of the electrolyte.

As described above, since the reference electrode including an electrolyte containing an optically-active material and the automatic electrochemical potential correction apparatus using the same according to the present invention are characterized in that the concentration of an electrode reaction material, such as $Cl^-$, in the electrolyte is calculated using the absorbance of the electrolyte solution containing the optically-active material, the change in potential of the reference electrode can be properly corrected even when the reference electrode is exposed to a test environment for a long period of time and thus the concentration of the electrolyte changes, so that the functions of the reference electrode can be maintained for a long period of time, thereby rapidly monitoring the abnormal states caused by damage to the reference electrode.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A reference electrode including an electrolyte containing an optically-active material, comprising:
    an electrode body provided at an end thereof with an electrolyte separation membrane and charged therein with an optically-active material and an electrolyte solution;
    an inner electrode disposed in the electrode body such that it is immersed in the electrolyte solution; and
    an absorbance measurement probe for transmitting light to the electrolyte solution and collecting reflected light waves, which is disposed in the electrode body such that it is immersed in the electrolyte solution.

2. The reference electrode according to claim 1, wherein the optically-active material is a material containing a chemical component absorbing one or more selected from among infrared light, visible light and ultraviolet light.

3. The reference electrode according to claim 1, wherein the absorbance measurement probe outputs light having a wavelength of 140~5000 nm.

4. The reference electrode according to claim 1, wherein the optically-active material is present in an initial concentration of 10 wt % or less.

5. The reference electrode according to claim 1, wherein the optically-active material is present in an initial concentration of 1.0 wt % or less.

6. The reference electrode according to claim 1, wherein the optically-active material is present in an initial concentration of 0.1 wt % or less.

7. The reference electrode according to claim 1, wherein the absorbance measurement probe is composed of one or more selected from among an optical fiber, an optical tube, an optical reflector, and an optical cell enabling light to permeate an electrolyte.

8. The reference electrode according to claim 1, wherein the inner electrode is made of one or more materials selected from among metals, conductive nonmetals, metal chlorides, metal oxides and metal sulfides.

9. The reference electrode according to claim 1, wherein the metal and conductive nonmetal include one or more selected from among silver (Ag), mercury (Hg), copper (Cu), platinum (Pt), gold (Au), nickel (Ni), titanium (Ti), zirconium (Zr), molybdenum (Mo), tungsten (W), glassy carbon and graphite.

10. An automatic electrochemical potential correction apparatus, comprising:
    a reference electrode including an electrode body provided at an end thereof with an electrolyte separation membrane and charged therein with an optically-active material and an electrolyte solution, an inner electrode disposed in the electrode body such that it is immersed in the electrolyte solution, and an absorbance measurement probe for transmitting light to the electrolyte solution and collecting reflected light waves, which is disposed in the electrode body such that it is immersed in the electrolyte solution;

a spectrometer for measuring absorbance by analyzing spectra of light waves collected by the absorbance measurement probe; and a reference potential corrector for outputting correction signals related to a change in the reference potential of the reference electrode according to the absorbance measured by the spectrometer.

11. The automatic electrochemical potential correction apparatus according to claim 10, wherein the optically-active material is a material containing a chemical component absorbing one or more selected from among infrared light, visible light and ultraviolet light.

12. The automatic electrochemical potential correction apparatus according to claim 10, wherein the absorbance measurement probe outputs light having a wavelength of 140~5000 nm.

13. The automatic electrochemical potential correction apparatus according to claim 10, wherein the optically-active material is present in an initial concentration of 10 wt % or less.

14. The automatic electrochemical potential correction apparatus according to claim 10, wherein the optically-active material is present in an initial concentration of 1.0 wt % or less.

15. The automatic electrochemical potential correction apparatus according to claim 10, wherein the optically-active material is present in an initial concentration of 0.1 wt % or less.

16. The automatic electrochemical potential correction apparatus according to claim 10, wherein the spectrometer measures the absorbance in a wavelength region of 150~2400 nm.

17. The automatic electrochemical potential correction apparatus according to claim 10, wherein the spectrometer measures the absorbance in a wavelength region of 200~1600 nm.

18. The automatic electrochemical potential correction apparatus according to claim 10, wherein the reference potential corrector calculates a change in concentration of the electrolyte using the absorbance measured by the spectrometer, and calculates the change of the reference potential due to the change in concentration of the electrolyte.

19. An automatic electrochemical potential correction apparatus, comprising:
a reference electrode including an electrode body provided at an end thereof with an electrolyte separation membrane and charged therein with an optically-active material and an electrolyte solution, and an inner electrode disposed in the electrode body such that it is immersed in the electrolyte solution;
a light source transmitting light to the reference electrode;
a light detector for collecting light waves emitted from the light source and passing through the electrolyte charged in the reference electrode;
a spectrometer for measuring absorbance by analyzing spectra of the light waves collected by the light detector; and
a reference potential corrector for outputting correction signals related to a change in the reference potential of the reference electrode according to the absorbance measured by the spectrometer.

20. The automatic electrochemical potential correction apparatus according to claim 19, wherein the light source outputs light having a wavelength of 140~5000 nm.

* * * * *